United States Patent [19]

Jensen et al.

[11] Patent Number: 4,892,878
[45] Date of Patent: Jan. 9, 1990

[54] OLEIC ACID ESTERS AND PHARMACEUTICAL COMPOSITIONS

[75] Inventors: Klaus G. Jensen, Frederiksberg; Peter Bregnedal, Allerod, both of Denmark

[73] Assignee: H. Lundbeck A/S, Copenhagen-Valby, Denmark

[21] Appl. No.: 124,819

[22] Filed: Nov. 24, 1987

[30] Foreign Application Priority Data

Dec. 3, 1986 [GB] United Kingdom ................. 8628903

[51] Int. Cl.⁴ .................. A61K 31/445; C07D 211/52
[52] U.S. Cl. .................................. 514/327; 514/225.8; 514/253; 544/45; 544/375; 546/222
[58] Field of Search ................... 544/45, 375; 546/222; 514/229.8, 253, 327

[56] References Cited

U.S. PATENT DOCUMENTS

| | | | |
|---|---|---|---|
| 3,194,733 | 7/1965 | Yale et al. | 514/225.8 |
| 3,350,268 | 10/1967 | Yale et al. | 514/225.8 |
| 3,681,346 | 8/1972 | Peterson et al. | 544/374 |
| 4,153,694 | 5/1979 | Buus et al. | 544/45 |

*Primary Examiner*—Richard L. Raymond
*Attorney, Agent, or Firm*—Gordon W. Hueschen

[57] ABSTRACT

The present invention relates to pharmaceutical compositions of novel oleic acid esters of wellknown neuroleptics and tranquillizers of the phenothiazine, thioxanthene and butyrophenone type containing an aliphatic hydroxy group, and which may be represented by the following general formula:

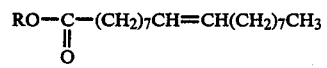

wherein R represents the residue of a hydroxy group containing neuroleptic selected from phenothiazines, thioxanthenes and butyrophenones, as well as pharmaceutically acceptable acid additions salts thereof, which compositions take the form of injectable solutions or suspensions in propylene glycol dioleate (TS-RD-9), methyl oleate or ethyl oleate.

None of the esters of Formula I have been specifically described before but have only been broadly disclosed in the patent literature, and the esters as such, as well as a method of preparation of said esters, fall within the scope of the present invention.

4 Claims, No Drawings

OLEIC ACID ESTERS AND PHARMACEUTICAL COMPOSITIONS

BACKGROUND OF THE INVENTION

Unesterified neuroleptics within the phenothiazine, thioxanthene and butyrophenone series have for a long time been used in the treatment of psychoses including schizophrenia; and also esters of higher alkanoic acids of said neuroleptics having five or more carbon atoms in the chain have been suggested and also widely used in the form of solutions in oils, mostly sesame oil and light vegetable oil, which have a sustained action when administered parenterally, preferably intramuscularly, showing a depot effect for up to four weeks (see for example U.S. Pat. Nos. 3,194,733, 3,350,268 and 3,681,346 and British Pat. Nos. 833,473 and 1,186,973).

So far, however, only enanthates and decanoates of the neuroleptics in question have been commercially available.

There has been a need therefore for very long acting preparations having great stability at room temperature for up to two years.

SUMMARY OF THE INVENTION

According to the present invention it has now surprisingly been found that these goals can be accomplished by solutions of the oleic acid esters of Formula I in TS-RD-9, methyl oleate or ethyl oleate.

The compositions of the present invention consists of sterile solutions or suspensions of an oleic acid ester of Formula I, or an acid addition salt thereof, in propylene glycol dioleate (TS-RD-9), methyl oleate or ethyl oleate. Such compositions may be injected parenterally into animals, including human beings, giving a duration of effect lasting for up to three months, and being particularly stable under normal conditions.

This invention also includes pharmaceutically acceptable salts of the oleic acid esters of Formula I formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether, with the desired salt separating directly. Exemplary of such organic salts are those with maleic, fumaric, benzoic, ascrobic, embonic, succinic, oxalic, bis methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

Especially preferred are the oleic acid esters of zuflupentixol (INN), and zuclopenthixol (INN), which are the pure (Z)-isomers.

Within the neuroleptic phenothiazines, the oleic acid esters of the wellknown neuroleptics fluphenazine (INN), periphenazine (INN), and pipotiazine (INN) are preferred according to the present invention.

Within the neuroleptic butyrophenones, especially the oleic acid ester of haloperidol (INN) is preferred.

The compositions may additionally contain gelling agents, e.g. aluminium stearate or other pharmaceutically acceptable adjuvants. Satisfactory neuroleptic action has been produced by a single intramuscular injection of about 20–500 mg of a neuroleptic of Formula I dissolved in TS-RD-9.

The preparation of the oleic acid esters of Formula I may according to the present invention be carried out according to methods wellknown in the art for the preparation of similar esters, comprising: reacting a hydroxy group containing neuroleptic of the phenothiazine, thioxanthene or butyrophenone type and oleic acid under conditions wellknown in the art for the preparation of peptides, e.g. in the presence of a coupling agent such as dicyclohexylcarbodiimide and an acylation catalyst; and isolating the compound of Formula I in the form of the free base or a pharmaceutically acceptable acid addition salt thereof.

The reaction is preferably carried out in an inert solvent, and as reactive derivatives of oleic acid are preferably used either the oleyl chloride or oleic acid anhydride.

When the compounds of Formula I are isolated as acid addition salts, preferably the hydrochlorides or dihydrochlorides are used, but other pharmaceutically acceptable salts may be used as well.

According to a preferred embodiment of the method of the invention a hydroxy group containing neuroleptic is reacted with oleic acid in the presence of dicyclohexylcarbodiimide and an acylation catalyst e.g. 4-dimethylaminopyridine in a solvent, e.g. methylene chloride.

Alternatively the novel compounds of Formula I may be prepared by reacting the hydroxy group containing neuroleptic with a reactive derivative of oleic acid, especially oleic acid chloride or bromide in an organic solvent, in wellknown manner, and isolating the ester formed as such or in the form of an acid addition salt thereof.

As examples of useful solvents may be mentioned pyridine, diethyl ether, $CH_2Cl_2$ and DMF.

As useful coupling agents may be mentioned dicyclohexylcarbodiimide, N,N-carbonyldiimidazole and diisopropylcarbodiimide.

Preferable acylation catalysts include 4-dimethylaminopyridine, 4-pyrrolidinopyridine or pyridine/p-toluenesulfonic acid.

The method according to the present invention shall be illustrated by the following examples which, however, may not be construed as limiting:

EXAMPLE 1

Zuflupentixol oleate.

To a suspension of 217 g (Z)-4-[3-[2-(trifluoromethyl)-9H-thioxanthen-9-ylidene] propyl]-1-piperazine ethanol, 113 g dicyclohexylcarbodiimide and 6 g 4-dimethylaminopyridine in 800 ml methylene chloride was added 142 g oleic acid in 200 ml methylene chloride. The resulting mixture was stirred overnight and dicyclohexyl urea filtered off. The filtrate was evaporated under reduced pressure, the resulting oil dissolved in 300 ml acetone and a solution of dry hydrogen chloride in diethyl ether added to pH 2–3. The resulting dihydrochloride was filtered and washed with diethyl ether. Mp 163°–165° C. The dihydrochloride was suspended in diethyl ether and treated with aquous ammonia.

The ether phase was washed with water, dried over anhydrous magnesium sulphate and evaporated at reduced pressure. The yield was 254 g of 9-(Z)-octadecenoic acid, 2-[4-[3-[2-(trifluormethyl)-9H-thioxanthen-9-yliden]propyl]-1-piperazinyl]ethyl ester as an oil. Content of free Zuflupentixol was estimated by TLC to be less than 0.1%.

The maleate melts at 172°–173° C.

The fumerate melts at 179°–181° C.

In a similar way was prepared:

Oleic acid, 2-[4-[3-[2-(trifluoromethyl)-10H-phenothiazin-10-yl]propyl]-1-piperazinyl]ethyl ester, (fluphenazine oleate) oil. Content of free fluphenazine was estimated by TLC to be less than 0.5%.

Oleic acid, 2-[4-[3-[2-chloro-10H-phenotiazin-10-yl]propyl]-1-piperazinyl]ethyl ester, (perphenazine oleate) oil. Content of free perphenazine was estimated by TLC to be less than 0.5%.

Oleic acid, (Z)-4-[3-[2-chloro-9H-thioxanthen-9-ylidene]propyl]-1-piperazinyl ethylester, (zuclopenthixol oleate) oil. Content of free Zuclopenthixol was estimated by TLC to be less than 0.2%.

EXAMPLE 2

Halperidol oleate

A mixture of 7 g of oleic acid and 6 g of oleyl chloride in 50 ml of pyridine was heated to 50° C. for 30 min. 3.8 g of haloperidol were added, and the resulting mixture was heated to reflux for 3 h and poured into ice. The mixture was extracted 3 times with ether, the organic phase was washed, first with water then with aqueous acetic acid, then with water again and, finally, with sodium carbonate solution. The ether phase was dried over anhydrous magnesium sulphate. Upon addition of 0.9 g of oxalic acid the oxalate crystallized. M.P. 130° C. The oxalate was suspended in ether and treated with aqueous ammonia. The ether phase was washed with water, dried over anhydrous magnesium sulphate and evaporated at reduced pressure. The yield was 3.1 g of 9-(2)-octadecenoic acid, 4-(4-chlorophenyl)-1-[4-(4-fluorophenyl)-4-oxobutyl]-4-piperidinyl ester, which was obtained as an oil.

The very long acting neuroleptic compositions of the present invention take the form of sterile solutions of a compound of Formula I in propylene glycol dioleate, (TS-RD-9), methyl oleate or ethyl oleate containing 2–10 mg of active ingredient per ml of final solution, preferably 10–50 mg of active ingredient.

The following examples of the neuroleptic compositions may serve to illustrate the invention:

| (1) | Zuflupentixol oleate | 20 g |
|---|---|---|
|  | Propylene glycol dioleate (TS-RD-9) | ad 100 ml |
| (2) | Zuclopenthixol oleate | 50 g |
|  | Propylene glycol dioleate (TS-RD-9) | ad 100 ml |
| (3) | Perphenazine oleate | 10 g |
|  | Propylene glycol dioleate (TS-RD-9) | ad 100 ml |
| (4) | Fluphenazine oleate | 20 g |
|  | Propylene glycol dioleate (TS-RD-9) | ad 100 ml |
| (5) | Zuflupentixol oleate | 5 g |
|  | Propylene glycol dioleate (TS-RD-9) | ad 100 ml |
| (6) | Zuclopenthixol oleate | 10 g |
|  | Propylene glycol dioleate (TS-RD-9) | ad 100 ml |
| (7) | Haloperidol oleate | 20 g |
|  | Propylene glycol dioleate (TS-RD-9) | ad 100 ml |

In the above examples the vehicle may be substituted with methyl- or ethyl oleate.

The compositions are prepared aseptically and filled into suitable containers such as ampoules or vials.

The invention also comprises a method for the alleviation, palliation mitigation, or inhibition of the manifestations of certain psychic abnormalities of animals by administering to a living animal body, including human beings, an adequate quantity of a composition according to the present invention. An adequate quantity would be from about 0.05 to about 5 mg per kilo of body weight in each injection dosis.

The long acting effect of compositions according to the present invention has been tested by administering the compositions intramuscularly into dogs and measuring the blood concentration of the active neuroleptic at certain intervals. Therapeutic effective concentrations were found up to 2–3 months after the injection.

In view of the very long intervals between the injections, the stability of the compositions of the invention is essential, and even after storage for two years at room temperature, concentrations of the active neuroleptic were lower than 1% of free neuroleptic compared with the total amount of neuroleptic in question.

It seems that such stability only will be obtainable if the compound of Formula I is administered in a lower aliphatic oleic acid ester, such as TS-RD-9, methyl oleate or ethyl oleate, as an administration in other vehicles such as the previously used sesame oil, light vegetable oil, olive oil, etc., will result in shorter duration of action. Moreover, such compositions are much less stable because of reesterification due to interaction between the oleic acid ester and the vehicle in question.

It is to be understood that the invention is not limited to the exact details of operation or exact compound or compositions shown and described, as obvious modifications and equivalents will be apparent to one skilled in the art.

We claim:

1. The oleic acid ester of 4-(4-(4-chlorophenyl)-4-hydroxy-1-piperidinyl)-1-(4-fluorophenyl)-1-butanone, as well as pharmaceutically acceptable acid addition salts thereof.

2. An injectable pharmaceutical composition containing as an active ingredient an oleic acid ester of claim 1, dissolved or suspended in propylene glycol dioleate (TS-RD-9), methyl oleate or ethyl oleate.

3. Method for the alleviation of psychic abnormalities in a subject in need thereof comprising the step of parenterally administering to the said subject a neuroleptically-effective amount of a compound of claim 1.

4. Method for the alleviation of psychic abnormalities in a subject in need thereof comprising the step of parenterally administering to the said subject a neuroleptically-effective amount of a composition of claim 2.

* * * * *